United States Patent [19]

Traynor

[11] 4,137,257

[45] Jan. 30, 1979

[54] TERPENE HYDROXYSULFONIC ACIDS AND CORRESPONDING HYDROXYSULFONATE SALTS

[75] Inventor: Sean G. Traynor, Jacksonville, Fla.

[73] Assignee: SCM Corporation, New York, N.Y.

[21] Appl. No.: 893,242

[22] Filed: Apr. 3, 1978

[51] Int. Cl.$^2$ .................. C07C 143/22; C07C 99/12; C11D 1/12
[52] U.S. Cl. .................................... 260/503; 252/555; 260/348.55; 260/458 C; 562/401
[58] Field of Search ............................ 260/503, 458 C

[56] References Cited

U.S. PATENT DOCUMENTS

| | | | |
|---|---|---|---|
| 2,174,505 | 9/1939 | Richmond | 260/503 |
| 3,277,163 | 10/1966 | Waldmann | 260/503 |
| 3,721,707 | 3/1973 | Straus et al. | 260/503 |

FOREIGN PATENT DOCUMENTS 398086  9/1933  United Kingdom ............... 260/503

Primary Examiner—Joseph E. Evans
Attorney, Agent, or Firm—Jerry K. Mueller, Jr.

[57] ABSTRACT

Optically active terpene hydroxysulfonate salts are made by sulfonating an optically active terpene epoxide of the p-menthane family, with a sulfonating agent selected from a sulfite, a bisulfite, or a thiosulfate.

21 Claims, No Drawings

TERPENE HYDROXYSULFONIC ACIDS AND CORRESPONDING HYDROXYSULFONATE SALTS

BACKGROUND OF THE INVENTION

The present invention relates to new optically active terpene hydroxysulfonic acids and hydroxysulfonate salts.

Preparation of sulfonic acid salts from a sulfite, a bisulfite, or a thiosulfate and an alkylene or cycloalkylene oxide is known. Such preparation can be found in Culvenor et al., *J. Chem. Soc.*, 278 (1949), Lauer & Hill, *J. Org. Chem.*, 58, 1873 (1936), and Lambert & Ross, *J. Chem. Soc.*, 46 (1949). It should be noted that in the foregoing citations, no useful products of the sulfonate salts have been proposed therein. The reaction of α- and β-carene oxides with sodium sulfite has been reported by E. Myslinski and E. Michalett, *Rocz. Chem.*, 41, 285–289 (1973) and 47, 1755–1758 (1973), to give hydroxysulfonate salts.

The optically active terpene hydroxysulfonic acids of this invention are prime candidates for resolving agents and their hydroxysulfonate salts are useful as surfactants, for example. Advantages in the process for their preparation include the preservation of the optical purity of the feed epoxide in the product sulfonate salt, and the substantial absence of racemization and isomerization products from the process.

BROAD STATEMENT OF THE INVENTION

The novel compounds of the present invention are hydroxysulfonates or hydroxysulfonic acids of an optically active terpene of the para-menthane family, their dehydration products and their oxidation products. The preferred synthesis of the optically active terpene hydroxysulfonate salts comprises maintaining an aqueous reaction mixture, and if desired an inert organic co-solvent, of an optically active terpene epoxide and a sulfonating agent selected from a sulfite, a bisulfite, or a thiosulfate at elevated temperature until the optically active terpene hydroxysulfonate salt is formed. The product sulfonate salt is substantially of the same optical purity as the feed epoxide. The terpene hydroxysulfonate salt then can be converted into the corresponding optically active terpene hydroxysulfonic acid by the addition, for example, of a proton donating acid to the terpene hydroxysulfonate salt. For the product terpene sulfonic acid to be a prime candidate as a resolving agent, the sulfonic acid preferably should contain an alternate functionality, such as an unsaturated group or oxygen-containing group (eg. an alcohol or ketone), within the molecule.

DETAILED DESCRIPTION OF THE INVENTION

The novel compounds of this invention are hydroxysulfonates or hydroxysulfonic acids of an optically active terpene of the para-menthane family, their dehydration products, and their oxidation products. As used herein, a terpene of the para-menthane family means a terpene having the carbon nucleus or skeleton of para-menthane, which skeleton can be substituted, eg. by hydroxyl, halogen, alkyl, nitrate, ether, aldehyde or the like, or could be unsaturated to varying degrees. The para-menthane skeleton can be represented conventionally as follows:

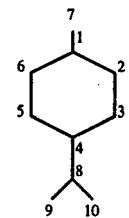

Nomenclature of the various para-menthane family members herein will follow the carbon numbering system indicated above.

The following list, though not exhaustive, represents suitable members of the para-menthane family included in the present invention:

para-menth-1-ene (carvomenthene), para-menth-3-ene,
para-mentha-1,8-diene (limonene), para-mentha-3,8-diene,
para-mentha-2,4-diene, para-mentha-1,5-diene (α-phellandrene), para-mentha-1(7),2-diene (β-phellandrene), para-mentha-2,4(8)-diene,
para-mentha-1(7), 8-diene (pseudolimonene),
para-menth-8-ene (dihydrodipentene),
para-menth-2-ene, para-mentha-2,8-diene (isolimonene),
para-mentha-1,4(8)-diene (terpinolene),
para-mentha-1,3-diene (α-terpinene),
para-mentha-1(7),4-diene (β-terpinene),
para-mentha-1,4-diene (γ-terpinene),
para-mentha-1(7),4(8)-diene and the like.

It should be noted that both the cis- and trans- isomers of the foregoing terpenes are included.

By way of illustration and not limitation, the following conventional structures show the hydroxysulfonates, hydroxysulfonic acids, their dehydration products, and their oxidation products derived from d-trans, and d-cis-para-menth-1-ene:

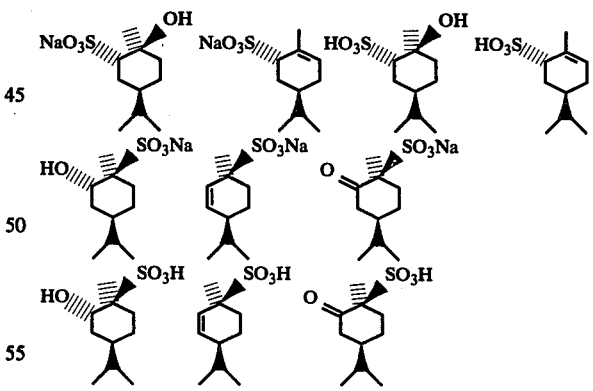

An expanded discussion of other sulfonate salts will be given below. Also, it must be recognized that the corresponding 1-trans and 1-cis compounds of the foregoing terpene hydroxysulfonate salts and hydroxysulfonic acids can similarly be conventionally written and are included in the present invention as are the corresponding families of compounds based on other members of the para-menthane family. While the term "hydroxysulfonate" or "hydroxysulfonic acid" of an optically active terpene of the para-menthane family is used herein, it also would be appropriate to describe such compounds as sulfonates or sulfonic acids of hydroxy terpenes, hydroxylated terpene sulfonates or sulfonic acids, or the like. Clearly, α-, β-hydroxysulfonate salts or hydroxysulfonic acids are intended. The chosen terminology used herein reflects in part the preferred method of preparing the instant compounds and accentuates the desired functionality which such compounds contain. Further on this will be given below.

As noted above, the preferred method of preparing the instant compounds involves the reaction of a terpene epoxide with a sulfonating agent selected from a sulfite, a bisulfite, or a thiosulfate. Referring to the terpene epoxide, an optically active unsaturated terpene can be formed into a terpene epoxide by a variety of conventional techniques which are well known in the art. One such technique is to add a peracid to a double bond contained in the terpene. Suitable peracids include perbenzoic acid, peracetic acid, trifluoroperacetic acid, and the like. Another conventional technique is to heat a terpene halohydrin in the presence of a base to form an epoxy group on the terpene. Still further techniques include conventional air blowing processes, including that process described in U.S. Pat. No. 3,014,047, which is incorporated herein expressly by reference, or by oxidation of an unsaturated terpene with a hydroperoxide, such as t-butyl hydroperoxide, in the presence of a transition metal catalyst, such as molybdenum hexacarbonyl. Of course, further techniques exist for synthesizing terpene epoxides suitable for feeding into the instant process and such techniques can be used as is necessary, desirable, or convenient.

Suitable optically active terpene epoxides for the process are the epoxides of optically active terpenes of the para-menthane family. Preferable of these epoxides include the cis- and trans-1,2-epoxides of para-menth-1-ene and limonene, and the cis- and trans-3,4-epoxides of para-menth-3-ene and para-menth-3,8-diene. The optically active terpene epoxides can contain groups or functionality capable of isomerizing under reaction conditions, e.g. a double bond, and be quite suitable for use in this process because in such process the occurrence of such isomerization is substantially precluded. Also, one need not worry about racemization of the terpene constituent of the product sulfonate salt because the process is designed to substantially preclude racemic products being formed from the optically active terpene epoxide fed to the process.

The sulfonating agent is selected from a sulfite, a bisulfite, or a thiosulfate. The sulfonating agent desirably is at least moderately water soluble for use in the aqueous reaction mixture. Advantageously, the sulfite, bisulfite, or thiosulfate is of an alkali metal, an alkaline earth metal, or ammonium, with sodium or potassium sulfite or bisulfite being preferred. Of course, the concentration of sulfonating agent in the aqueous reaction mixture may be limited by its water solubility at a chosen reaction temperature, though other reaction parameters, such as, for example, terpene epoxide concentration in a final volume of the reaction mixture, can be adjusted accordingly in order to compensate therefor.

The process is conducted by forming an aqueous reaction mixture of the terpene epoxide and sulfonating agent. Advantageously, the sulfonating agent is used in a molar excess over the terpene epoxide, though broadly the molar ratio of the terpene epoxide to sulfonating agent ranges between about 0.1 and about 10.0. The aqueous reaction mixture contains at least about 1.0% water, although non-participating organic solvents such as hindered alcohols, e.g. t-butanol, ethers, certain ketones, quaternary ammonium or other phase transfer agents and the like, can be added to the aqueous reaction mixture as is necessary or desirable. The aqueous reaction mixture is heated to reflux temperature or elevated temperatures under pressure. Advantageous temperatures for conducting the reaction are from about 40° to about 200° C. and the reaction mixture is heated for about 0.1 to about 200 hours until the sulfonate salt is formed, though it is conceivable that reaction could take place in as little as a few minutes in a continuously fed tubular reactor.

The optically active hydroxysulfonate salt can be recovered (typically in hydrated form) and used in this form, or it can be converted into a sulfonic acid by the addition of a proton donating acid. Suitable protic acids include, for example, hydrochloric acid, sulfuric acid, formic acid and the like, though the stronger acids are decidedly preferred. Careful acidification of the tertiary hydroxy products or products containing double bonds is required if dehydration or double bond isomerization is not desired. Additionally, the sulfonate salt can be converted into its sulfonic acid by conventional acid ion-exchange chromatography. As was mentioned above, a unique feature of the process is that the optical purity of the terpene epoxide is preserved in the sulfonate salt produced by the process. Furthermore, virtually no racemization or isomerization of the terpene sulfonate salt takes place during the reaction so that the desired optically active hydroxysulfonate salt or hydroxysulfonic acid can be produced in good yield and purity by the process.

The optically active terpene sulfonic acids derived from the present process can be used as resolving agents. When making terpene sulfonic acid candidates for ascertaining their ability to resolve optically active compounds, such as pharmeceuticals and their intermediates, for example, it is desirable that there be an asymmetric carbon atom near the sulfonic acid group. It is also desirable that there be an electron-rich site contained in the terpene portion of the terpene sulfonic acid. Such electron-rich sites can be a double bond (e.g. dehydration products of the terpene hydroxysulfonic acids) or an oxygen atom in the form of a hydroxyl group or carbonyl group (e.g. oxidation products of the terpene hydroxysulfonic acids), for example. While not all sulfonic acids made by the instant process have been shown to be suitable for use as resolving agents, those optically active terpene hydroxysulfonic acids having the requisite asymmetric carbon atom and additional electron-rich functionality contain characteristics generally agreed desirable of resolving agents, for example, camphor-10-sulfonic acid.

Dehydration products of the instant hydroxysulfonates and hydroxysulfonic acids of optically active terpenes of the para-menthane family can be prepared in conventional fashion. Thus, one may conduct the dehydration reaction, with acids, such as sulfuric acid or phosphoric acid; anhydrides, such as phosphorus pentoxide or phthalic anhydride; or, perhaps, in the vapor phase over aluminum oxide, for example. Dehydration of the tertiary alcohol sulfonates and sulfonic acids is preferred for convenience and especially when a resolving agent candidate is being prepared. Such tertiary alcohol dehydration products are β-γ-unsaturated sulfonates or sulfonic acids or alkyl sulfonic acid esters (preferably a $C_1$–$C_{10}$ alkyl group) of the terpene.

Oxidation products of the instant hydroxysulfonates and sulfonic acids can be classified as $\beta$-keto-sulfonate salts or sulfonic acids or alkyl sulfonic acid esters (preferably a $C_1$-$C_{10}$ alkyl group), and their preparation is conventional. Thus, it is possible to employ strong oxidizing agents, such as an acid dichromate, potassium permanganate, manganese oxide, chromate-pyridine complexes, lead tetraacetate in pyridine, and the like; dehydrogenation catalysts, such as, copper chromite; or conduct an Oppenauer oxidation.

The following Examples show in detail how the invention can be practiced but should not be construed as limiting. In this application, all degrees are in degrees Centigrade, all ratios are molar ratios, and all percentages are molar percentages, unless otherwise expressly indicated. Also, satisfactory IR, $H^1$NMR, and $C^{13}$NMR results were obtained for all of the compounds prepared in the examples.

EXAMPLE 1

Into a 3 liter flask equipped with a high speed mechanical stirrer was charged (+)trans-menthene-1,2-oxide (0.86 moles), sodium sulfite (0.91 moles), and water (800 ml). The reaction mixture was vigorously stirred during reflux for 16 hours until there was no longer an oil layer present. Evaporation of the solvent in vacuo gave a white solid which was washed twice with diethyl ether. The ether extracts contained 15.8 g of mostly (+)-trans-1-hydroxyneocarvomenthol. Recrystallization of the remaining solid (225 grams) from 90% ethanol gave 153 grams (60.5% theory yield based on dihydrate) of the white crystalline (+)trans-1-hydroxy-p-menthane-2-sulfonic acid sodium salt. Mp=195-200° C., $[\alpha]_D$=+15.5° (C=10) $H_2O$. Found: C=40.70, H=7.80, S=11.0, Na=7.56%. Calculated for dihydrate, $C_{10}H_{23}SO_6Na$; C=40.80, H=7.88, S=10.89, Na=7.81%.

EXAMPLE 2

(+)-trans-Menthene-1,2-oxide (4.0 moles) was refluxed with stirring for 40 hours in water (2 liters) containing sodium sulfite (6.0 moles). A white crystalline solid precipitated upon cooling. The reaction mixture was washed with diethyl ether which removed 43.8 g of the solid diol hydrate. Recrystallization of the sodium sulfonate from 90% ethanol yielded 749 grams (63.6% theory yield) of pure product.

EXAMPLE 3

(30)-trans-Limonene-oxide (0.658 moles) was refluxed for 18 hours with sodium sulfite (0.952 moles) in water (400 ml) with stirring. Ether extraction of the cooled reaction mixture gave 10.6 g of the hydrated diol. Recrystallization of the crude sulfonate salt from 90% ethanol gave 76.3 g (40.3% theory yield based on dihydrate) of a white crystalline solid identified as the trans-1-hydroxy-p-menth-8,9- ene-2-sulfonic acid sodium salt. Mp=205°-215° C. dec., $[\alpha]_D$=+50° (C=4) $H_2O$. Found: C=46.91, H=6.81, S=12.33, Na=8.91%. Calculated for $C_{10}H_{17}SO_4Na$:C=46.86, H=6.69, S=12.51, Na=8.97%.

EXAMPLE 4

(+)-cis-Menthene-1,2-oxide (1.79 moles) was refluxed for 80 hours in water (1200 ml) containing sodium sulfite (3.6 moles) and Aliquot 336 phase transfer reagent (1 ml). After removal of the diol (69.2 g), the crude hydroxysulfonate was recrystallized from ethanol and gave 185 g (40% theory yield based on non-hydrated product) of the pure white crystalline (−)trans-2-hydroxy-p-menthane-1-sulfonic acid sodium salt. Mp=213°-216° C. $[\alpha]_D$=−5.2° (C=20)$H_2O$; (+)phenylglycine salt, Mp=190°-194° C., $[\alpha]_D$=−48.2° (C=8.5) $H_2O$. Found: C=56.06, H=7.49, N=3.74, S=8.03%. Calculated for $C_{18}H_{29}SO_6Na$: C=55.79, H=7.54, N=3.62, S=8.28%.

EXAMPLE 5

(+)-cis-Menthene-1,2-oxide (4.8 moles) was refluxed for 111 hours in water (2400 ml) containing sodium sulfite (7.2 moles). After 50 hours, tetrabutylammonium bromide (1 g) was added to the reaction mixture. Ether extraction removed 141 g of diol. Recrystallization of the crude sulfonate salt from 90% ethanol yielded 548 g (44.2% theory yield) of pure product.

EXAMPLE 6

(+)-cis-Limonene oxide (0.658 moles) was heated in a Parr bomb containing water (400 ml), sodium sulfite (0.952 moles), and tetrabutylammonium bromide (0.003 moles) for 18 hours at 150° C. (65 psig). Extraction of the cooled solution with ether gave 36.2 g of diol. Recrystallization of the crude hydroxysulfonate from 90% ethanol yielded 53.6 g (27.9% theory yield, based on dihydrate) of pure white crystalline trans-2-hydroxy-p-menth-8,9-ene-1-sulfonic acid sodium salt. Mp=250°-260° C., Found: C=40.94, H=7.32, S=11.22, Na=7.61%. Calculated for dihydrate, $C_{10}H_{21}SO_6Na$: C=41.08, H=7.24, S=10.97, Na=7.87%.

EXAMPLE 7

A mixture of (+)-limonene-8,9-oxides (2.64 moles) was refluxed, with stirring, for 15 hours with sodium sulfite (5.0 moles) in water (1500 ml). Ether extraction yielded 50.1 g of the diol. Recrystallization of the crude sulfonate from 90% ethanol gave 462 g. (68% theory yield based on non-hydrated product) of the diasteriomeric (+)-8-hydroxy-p-menthane-9-sulfonic acid salts. Mp=205°-215° C. dec., $[\alpha]_D$=+50° (C=4) $H_2O$. Found C=46.91, H=6.81, S=12.33, Na=8.91%. Calculated for $C_{10}H_{17}SO_3Na$: C=46.86, H=6.69, S=12.51, Na=8.97%.

EXAMPLE 8

(+)-trans-1-Hydroxy-p-menthane-2-sulfonic acid sodium salt (1.7 moles) was refluxed for 22 hours with acidic Amberlyst-15 ion exchange resin in water (1200 ml). The reaction mixture was filtered and basified with sodium hydroxide. Evaporation of the water in vacuo gave a crude white sulfonate salt. Recrystallization from 95% ethanol yielded 230 g. (48.3% theory yield based on dihydrate) of p-menthene-6-sulfonic acid sodium salt.

EXAMPLE 9

(−)-trans-2-Hydroxy-p-menthane-1-sulfonic acid sodium salt (0.092 moles) in 90% ethanol was passed through an ion exchange column in the acid form (ANGC-242). Evaporation of the solvent yielded the oily sulfonic acid which was dissolved in water (90 ml) and to this was added (±)-phenylglycine (0.066 moles). The reaction mixture was heated, filtered, and the filtrate allowed to stand at room temperature overnight. Filtration gave the crystalline adduct (5.6 g), mp=190°-194° C., $[\alpha_D]$ =−48.23° (C=8.5) $H_2O$. To the adduct (2.0 g) in water (50 ml) was carefully added ammonium hydroxide until pH=8 was reached. Filtration of the resulting white solid gave (+)phenylglycine (0.37) $[\alpha]_D = +154.5°$ (1.22N HCl).

EXAMPLE 10

(−)-trans-2-Hydroxy-p-menthane-1-sulfonic acid (0.046 moles) was prepared by the procedure of Example 9. The oily sulfonic acid was dissolved in water (50 ml) to which was added (±) phenylglycine (0.046 moles). The reaction mixture was heated to boiling and filtered to remove unreacted phenylglycine. After standing at room temperature for two hours, a white crystalline needle precipitate was filtered (4.6 g). A portion of this product (2.0 g) was dissolved in water (50 ml) and the pH adjusted to 8 with a concentrated ammonia solution. Filtration of the precipitate gave (+)-phenylglycine (0.5 g) $[\alpha]_D = +154°$ (C=5) 1.00N HCl. Optically pure phenylglycine is reported by Clark et al (J. Chem. Soc., Perkin 1, 473 (1976) as ±158.6°±0.8° in 1.00N HCl.

I claim:

1. A compound containing the saturated or non-aromatically unsaturated, carbon skeleton of para-menthane, said skeleton containing adjacently a hydroxyl group and a sulfonate salt or sulfonic acid group; the unsaturated sulfonate salt or sulfonic acid dehydration products of said compound; the β-keto-sulfonate salt or sulfonic acid oxidation products of said compound; and the $C_1$–$C_{10}$ alkyl esters of said unsaturated sulfonic acid or said β-keto-sulfonic acid.

2. The compound of claim 1 wherein said carbon skeleton is mono-unsaturated.

3. The compound of claim 1 wherein said sulfonate salt is a sulfonic acid salt of an alkali metal, an alkaline earth metal, or ammonia.

4. The compound of claim 3 wherein said sulfonate salt is a sulfonic acid salt of sodium or potassium.

5. A racemic mixture of optical isomers of the compound of claim 1.

6. The compound of claim 1 which is substantially optically pure.

7. The compound of claim 1 wherein said carbon skeleton of paramenthane is represented by

and said hydroxyl group and said sulfonate salt or sulfonic acid group is attached to one of the following pairs of carbon atoms in either order: $C_1$–$C_2$, $C_2$–$C_3$, $C_3$–$C_4$, or $C_8$–$C_{10}$.

8. The compound of claim 7 wherein said pairs of carbon atoms are $C_1$–$C_2$ and said carbon skeleton contains unsaturation at one of the following carbon atom pairs: $C_3$–$C_4$, $C_4$–$C_5$, $C_5$–$C_6$, $C_4$–$C_8$, or $C_8$–$C_{10}$.

9. The compound of claim 7 wherein said pairs of carbon atoms are $C_2$–$C_3$ and said carbon skeleton contains unsaturation at one of the following carbon atom pairs: $C_4$–$C_5$, $C_4$–$C_8$, or $C_8$–$C_{10}$.

10. The compound of claim 7 wherein said pairs of carbon atoms are $C_3$–$C_4$ and said carbon skeleton contains unsaturation at the following carbon atom pair: $C_8$–$C_{10}$.

11. The compound of claim 1 wherein said carbon skeleton of paramenthane is represented by

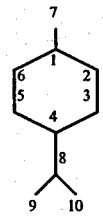

and said hydroxyl group and said sulfonate salt or sulfonic acid group is attached to one of the following pairs of carbon atoms, in either order, and the other pair of carbon atoms is unsaturated or has said hydroxyl group and said sulfonate salt or sulfonic acid group attached thereto, in either order, said pairs of carbon atoms selected from: $C_1$–$C_2$, $C_3$–$C_4$; $C_1$–$C_2$, $C_4$–$C_5$; $C_1$–$C_2$, $C_5$–$C_6$; $C_1$–$C_2$, $C_4$–$C_8$; $C_1$–$C_2$, $C_8$–$C_{10}$; $C_2$–$C_3$, $C_4$–$C_5$; $C_2$–$C_3$, $C_4$–$C_8$; $C_2$–$C_3$, $C_8$–$C_{10}$; $C_3$–$C_4$, $C_8$–$C_{10}$; $C_1$–$C_7$, $C_2$–$C_3$; $C_1$–$C_7$, $C_4$–$C_5$; $C_1$–$C_7$, $C_4$–$C_8$; and $C_1$–$C_7$, $C_8$–$C_{10}$.

12. The unsaturated sulfonate salt or sulfonic acid dehydration products of the compound of claim 7.

13. The unsaturated sulfonate salt or sulfonic acid dehydration products of the compound of claim 8.

14. The unsaturated sulfonate salt or sulfonic acid dehydration products of the compound of claim 9.

15. The unsaturated sulfonate salt or sulfonic acid dehydration products of the compound of claim 10.

16. The unsaturated sulfonate salt or sulfonic acid dehydration products of the compound of claim 11.

17. The β-keto sulfonate salt or sulfonic acid oxidation products of the compound of claim 7.

18. The β-keto sulfonate salt or sulfonic acid oxidation products of the compound of claim 8.

19. The β-keto sulfonate salt or sulfonic acid oxidation products of the compound of claim 9.

20. The β-keto sulfonate salt or sulfonic acid oxidation products of the compound of claim 10.

21. The β-keto sulfonate salt or sulfonic acid oxidation products of the compound of claim 11.

* * * * *

UNITED STATES PATENT AND TRADEMARK OFFICE
CERTIFICATE OF CORRECTION

PATENT NO. : 4,137,257
DATED : Jan. 30, 1979
INVENTOR(S) : Sean G. Traynor

It is certified that error appears in the above-identified patent and that said Letters Patent are hereby corrected as shown below:

Column 5, line 50, Example 3, change "(30)" to --(+)--.
Column 8, lines 6 and 7, in claim 9, "cottains" should have been --contains-- but it is misspelled in the original specification also.

Signed and Sealed this

Seventeenth Day of July 1979

[SEAL]

Attest:

LUTRELLE F. PARKER
Attesting Officer     Acting Commissioner of Patents and Trademarks